US007005561B2

(12) United States Patent
Parrott et al.

(10) Patent No.: US 7,005,561 B2
(45) Date of Patent: Feb. 28, 2006

(54) ARABITOL OR RIBITOL AS POSITIVE SELECTABLE MARKERS

(75) Inventors: Wayne Parrott, Athens, GA (US); Peter LaFayette, Watkinsville, GA (US); Patrick Kane, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 158 days.

(21) Appl. No.: 09/802,208

(22) Filed: Mar. 8, 2001

(65) Prior Publication Data

US 2003/0041352 A1 Feb. 27, 2003

Related U.S. Application Data

(60) Provisional application No. 60/188,291, filed on Mar. 8, 2000, and provisional application No. 60/225,595, filed on Aug. 15, 2000.

(51) Int. Cl.
*C12N 15/82* (2006.01)
*C12N 15/74* (2006.01)
*C12N 15/90* (2006.01)
*A01H 5/10* (2006.01)

(52) U.S. Cl. .................... 800/288; 435/419; 435/468; 435/471; 435/483; 435/484; 536/23.7; 800/298

(58) Field of Classification Search ............. 435/320.1, 435/410, 419, 468, 471, 483, 484; 536/23.7; 800/278, 288, 295, 298
See application file for complete search history.

(56) References Cited

U.S. PATENT DOCUMENTS

| | | | |
|---|---|---|---|
| 4,857,467 A | 8/1989 | Sreekrishna et al. | ...... 435/255.1 |
| 5,011,909 A | 4/1991 | Borovsky et al. | ............ 530/328 |
| 5,130,253 A | 7/1992 | Borovsky et al. | ........ 435/320.1 |
| 5,223,419 A | 6/1993 | Katagiri et al. | ............. 800/208 |
| 5,254,801 A | 10/1993 | Dotson et al. | ............... 800/278 |
| 5,767,378 A | 6/1998 | Bojsen et al. | ............... 800/278 |

FOREIGN PATENT DOCUMENTS

| WO | WO 942627 | 9/1994 |
|---|---|---|
| WO | WO 974448 A | 11/1997 |

OTHER PUBLICATIONS

Sung et al., Plant Cell Physiol., 1997, vol. 38, pp. 484–489.*
Bartkus, J.M. et al., *Construction of an Improved D–Arabinose Pathway in Escherichia Coli K–12*, Journal of Bacteriology, Washington, D.C. 165:3, 704–709, 1986.
Brunker, P. et al., *Structure and function of the genes involved in mannotol, arabitol, and glucitol utilization from Pseudomonas fluorescens DSM50106* Gene 117–126 (1998).
Heuel H, Shakeri–Garakani A, Turgut's Lengeler JW, *Genes for D–arabinitol and ribitol catabolsim from Klebsiella pneumoniae*, Microbiology 144:1631–1639 (1998).

Heuel H, Turguts, Schmid K, Lengeler JW, *Substrate recognition domains as revealed by active hybrids between the D–arabitol and ribitol transporters from Klebsiella pneumoniae*. J Bacteriol 179:6014–6019 (1997).
Lafayette, P.F. & Parrott, W.A., *A non–antibiotic marker for amplification of plant transformation vectors in E. coli.* Plant Reports, 20:338–342, 2001.
Link, C.D. et al., *Genotypic Exclusion: A Novel Relationship Between the Ribitol–Arabitol and Galactitol Genes of E. Coli*, Molecular and Genral Genetics, Spinger Verlag, Berlin DE, 189:337–339, 1983.
Link, C.D. et al., *Inverted Repeats Surround the Ribitol–Arabitol Genes of E. Coli C*, Nature, 298, 94–96, 1982.
Loviny T. et al., *Ribitol Dehydrogenase of Klebsiella–Aerogenes Sequence of the Structural Gene* Biochem J. 230, 579–585 (1985).
Postma, P.W. et al., *Phosphoenolpyruvate: Charbohystrate Phosphotransferase Systems of Bacteria*, Microbiological Reviews, American Society for Microbiology, Washington, D.C. 57:3, 543–594, 1993.
Reiner AM, *Genes for ribitol and D–arabitol catabolism in Escherichia coli: their loci in C strains and absence in K–12 and B strains*. J Bacteriol 123:530–536 (1975).
Scangos, G. A. et al., *Ribitol and D–Arabitol Catabolsim in Escherichia Coli*, Journal of Bacteriology Washington, D.C. 134:2, 492–500 1978.
Trimbur, D.E. et al., *Isolation and Characterization of Escherichia Coli Mutatns Able to Utiliza the Novel Pentose L–Ribose*, Journal of Bacteriology, Washington, D.C., 173:8, 2459–2464 1991.
Wong, B. et al., *D–Arabitol Metabolism in Candida Albicans: Studies of the Biosythentic Pathway and the Gene that Encodes NAD Dependent D–Arabitol Dehydrogenase*, Journal of Bacteriology, Washington, D.C. 175:19, 6314–6320 1993.

(Continued)

Primary Examiner—Ashwin Mehta
(74) Attorney, Agent, or Firm—Timothy H. Van Dyke; Beusse Brownlee Wolter; Mora & Maire (57) ABSTRACT

Disclosed herein are novel methods and materials for selecting transgenic cells. Specifically exemplified herein are positive selection methods that involve conferring to cells the ability to metabolize certain compounds, preferably arabitol, ribitol, raffinose, sucrose, mannitol or combinations thereof. Accordingly, transformed cells can be selected by simply subjecting them to a medium containing such compounds. The subject invention alleviates the disadvantages and concerns of negative selection methods, such as the unnecessary killing of transformed cells and the dispersal of potentially harmful genes (e.g., antibiotic or herbicide resistant genes) into the environment. Furthermore, novel nucleotide sequences relating to the *E. coli* rtl operon and arabitol dehydrogenase gene, and amino acid sequences relating to the gene products thereof are disclosed.

23 Claims, 2 Drawing Sheets

OTHER PUBLICATIONS

Stewart, Neal C. et al., *Genetic Transformation, Recovery and Characterization of Fertile Soybean Transgenic for a Synthetic Bacillus thurnigensis cryIAc Gene*, Plant Physiol 112: 121–129, 1996.

Atschul, S. F. et al., *Basic Local Alignment Search Tool*, J. Mol. Biol. 215:403–410 (1990).

Bachmann B.J., *Pedigrees of Some Mutant Strains of Escherichia coli K–12*. Bacteriol Rev 36:525–557 (1972).

Bailey et al., *Genotype Effects on Proliferative Embryogenesis and Plant Regneration of Soybean*, In Vitro–Plant. 29P:102–108 (Jul. 1993).

Haldrup, A., Petersen, S. & Okkels, F. *Positive selection: A plant selection principle based on xylose isomerase, an enzyme used in the food industry*. Plant Cell Rep. 18, 76–81. (1998).

Kanabus, J., Bressan, R. & Carpita, N. *Carbon assimilation in carrot cells in liquid culture.* Physiol. Plant. 82, 363–368 (1986).

Klein TM, Wolf Ed, Wu R, Sanford JC *High–velocity microprojectiles for delivering nucleic acids into living cells*. Nature 327:70–73 (May 1987).

Linn, E. *An inducible D–arabitol dehydrogenase from Aerobacter aerogenes*. J. Biol. Chem. 236, 31–36 (Jan. 1961).

Odell et al., *Identification of DNA sequences required for activity of the cauliflower mosaic virus 35S promoter*. Nature 313:810–812 (Feb. 1985).

Tartof, K.D., C.A.Hobbs, *Improved media for growing plasmid and cosmid clones*. Focus 9:12–16 (1987).

Wiman M, Bertani, G, Kelly B, Sasaki I *Genetic map of Escherichia coli strain C*. Mol Gen Genet 107:1–31 (1970).

Zheng Z, Hayashimoto A, Liz, Murai N, *Hygromycin resistance gene cassettes for vector construction and selection of transformed rice protoplasts*. Plant Physiol 97:832–835 (1991).

Bailey et al., *Genotype–specific optimization of plant regeneration from somatic embryos of soybean*, Plant Science 93:117–120 (1993).

Christou et al., *Stable Transformation of Soybean Callus by DNA–Coated Gold Particles*, Plant Physiology 87:671–674 (1988).

Samoylov et al., *Soybean [Glycine Max (L) Merrill] Embryogenic Cultures: The role of Sucrose and Total Nitrogen Content on Proliferation*. In Vitro Cell Dev.Biol.—Plant 34:8–13 (Mar. 1998).

Samoylov et al., *A liquid–medium–based protocol for rapid regeneration from embryogenic soybean cultures*. Plant Cell Rep 18:49–54 (1998).

Viola, R. *Hexose metabolism in discs excised from developing potato (Solanum tuberosum L) tubers. II. Extimations of fluxes in vivo and evidence that fructokinase catalyses a near rate–limiting reaction*. Planta 198. 186–196, (1996).

* cited by examiner

ARABITOL OR RIBITOL AS POSITIVE SELECTABLE MARKERS

CROSS-REFERENCE TO RELATED APPLICATIONS

This application claims the benefit under 35 USC §119(e) of Provisional Application Nos. 60/188,291 filed Mar. 8, 2000 and 60/225,595 filed Aug. 15, 2000.

BACKGROUND OF THE INVENTION

The term "transformation" is generally understood in the biotech and chemical arts to refer to a stable incorporation of a foreign DNA or RNA into a cell which results in a permanent, heritable alteration in the cell. It is well known that when new genetic material is to be introduced into a population of cells by transformation, only a certain number of the cells are successfully transformed. It is then necessary to identify the genetically transformed cells so that these cells can be separated from the non-transformed cells of the population. Identification and separation of the transformed cells has traditionally been accomplished using "negative selection", whereby the transformed cells are able to survive and grow, while the non-transformed cells are subjected to growth inhibition or perhaps even killed by a substance which the transformed cells, by virtue of their transformation, are able to tolerate.

For example, when a population of plant cells is transformed, selection of the transformed cells typically takes place using a selection gene which codes for antibiotic or herbicide resistance. The selection gene—which in itself generally has no useful function in the transformed plant (and may in fact be undesirable in the plant) is coupled to or co-introduced with the desired gene to be incorporated into the plant, so that both genes are incorporated into the population of cells, or rather into certain of the cells in the population, since it is difficult, if not impossible, in practice to transform all of the cells. The cells are then cultivated on or in a medium containing the antibiotic or herbicide to which the genetically transformed cells are resistant by virtue of the selection gene, thereby allowing the transformed cells to be identified, since the non-transformed cells—which do not contain the antibiotic or herbicide resistance gene in question—are subjected to growth inhibition or are killed.

These negative selection methods have, however, certain disadvantages. First of all, the non-transformed cells may die because of the presence of antibiotics or herbicides in the growth medium. As a result, when the population of cells is a coherent tissue there is a risk that not only the non-transformed cells but also the transformed cells may die, due to the fact that the death of the non-transformed cells may cut off the supply of nutrients to the transformed cells or because the damaged or dying non-transformed cells may excrete toxic compounds.

Another disadvantage of negative selection is that the presence of an unnecessary gene, for example antibiotic resistance, may be undesirable. There is concern among environmental groups and governmental authorities about whether it is safe to incorporate genes coding for antibiotic resistance into plants and microorganisms. This concern is of particular significance for food plants and for microorganisms which are not designed to be used in a closed environment (e.g. microorganisms for use in agriculture), as well as for microorganisms which are designed for use in a closed environment, but which may accidentally be released therefrom.

Positive selection is a selection system whose operating principle is converse to negative selection. Rather than conferring resistance to a negative or toxic substance, positive selection involves conferring onto the transformed cell a metabolic, or other, competitive advantage over nontransformed cells. Positive selection systems identify and select genetically transformed cells without damaging or killing the non-transformed cells in the population and without co-introduction of antibiotic or herbicide resistance genes. As alluded to above, there is increasing concern that genes conferring resistance to antibiotics and/or herbicides may disperse and be incorporated into agriculturally destructive weeds and other plants, as well as pathogenic bacteria. Indeed, transgenic plants have been banned in the European Union. As a result, more and more investigative efforts are being made to develop positive selection systems for use in plants and other cell types.

SUMMARY OF THE INVENTION

The subject invention relates to a positive selection system that involves conferring to transferred cells the ability to metabolize arabitol, ribitol, and/or mannitol. One aspect of the subject invention pertains to a gene construct comprising a gene of interest and a selectable marker gene. A specific aspect pertains to supplying to a population of cells at least one marker compound which is directly or indirectly active in the transformed cells containing the gene of interest and is inactive or less active in the non-transformed cells whereby the transformed cells are provided with a selective advantage. Alternatively, the selective advantage is one wherein the expression of the gene of interest or the positive selecting gene leads to an increase in the activity of an enzyme found endogenously in the population of cells such that the activity of the enzyme in the transformed cells is greater than the activity of the enzyme in non-transformed cells.

According to a further aspect, the marker compound supplied to the population of cells is selected from the group consisting of arabitol, ribitol, mannitol or a derivative or variant thereof.

A further aspect pertains to transformed cells selected according to the above-recited method. Moreover, an additional aspect pertains to plants derived from said transformed cells.

According to an alternative aspect, the invention includes both positive selection and negative selection including the use of a gene coding for antibiotic or herbicide resistance.

Yet a further aspect of the invention relates to genetically transformed cells comprising a gene of interest and selectable marker gene wherein the selectable marker gene induces a positive effect in the transformed cells and gives said cells a selective advantage when a population of cells including the transformed cells and nontransformed cells is supplied with a compound.

Moreoever, another aspect of the invention includes a method of selecting genetically transformed cells from a population of cells comprising a) introducing into the genome of a cell a gene of interest and a selectable marker gene;

b) obtaining transformed cells;

c) supplying to the population of cells a marker compound wherein said transformed cells have a selective advantage over non-transformed cells due to expression or transcription of the gene of interest or the selectable marker gene in the presence of the marker compound; and d) selecting said transformed cells from the population of cells wherein said selectable marker gene comprises a ribitol or D-arabitol dehydrogenase, a ribitol or D-arabitol kinase, a ribitol or D-arabitol transporter gene, or a combination thereof, and the compound is arabitol, ribitol or a derivative precursor thereof.

Further still, an additional aspect of the subject invention pertains to polynucleotide molecules that encode proteins having the biological activity of ribitol or arabitol dehydrogenase, ribitol or arabitol kinase, ribitol or arabitol transporter, or ribitol or arabitol repressor. Specifically, the aspect pertains to a polynucleotide as shown in SEQ ID NOS: 1 and 2, or functional fragments and variants thereof. Furthermore, another aspect of the subject invention pertains to a polypeptide encoded by the polynucleotide molecules of the subject invention.

A further aspect of the subject invention pertains to cells transformed with the polynucleotide molecules of the subject invention. Specifically exemplified are transformed bacteria, fungi, yeast, animal and plant cells. More specifically exemplified are transformed bacteria and plant cells.

These and other advantageous aspects of the subject invention are described in further detail below.

BRIEF DESCRIPTION OF THE SEQUENCES

SEQ ID NO:1 represents the nucleotide sequence of the arabitol dehydrogenase gene from *E. coli* strain C.

SEQ ID NO: 2 represents a polynucleotide molecule which comprises a nucleotide sequence encoding the rtl operon from *E. coli* strain C. Bases 96 to 848 encode for ribitol dehydrogenase. Bases 859 to 2463 encode for ribitol kinase. Bases 2565 to 3839 encode for ribitol transporter.

SEQ ID NO: 3 represents the amino acid sequence of *E. coli* strain C ribitol dehydrogenase.

SEQ ID NO: 4 represents the amino acid sequence of *E. coli* strain C ribitol kinase.

SEQ ID NO: 5 represents the amino acid sequence of *E. coli* strain C ribitol transporter.

DETAILED DISCLOSURE OF THE INVENTION

The term "gene of interest" as used herein refers to any nucleotide sequence, which is to be incorporated into the cells to produce genetically transformed cells. Introduction of nucleotide sequence into plants, microorganisms and animals is widely practiced, and there are no limitations upon the nucleotide sequences whose presence may be detected by use of the positive selection method described herein. By use of the subject methods the presence of the gene of interest in the genetically transformed cells may be determined without the above-mentioned disadvantages associated with traditional negative selection systems.

The term "selectable marker gene" refers to any nucleotide sequence that is preferably co-introduced with a gene of interest, wherein a selective advantage is conferred to a cell transformed with said selectable marker gene.

In a preferred embodiment, the gene of interest is directed to one or more functional genes that are chosen to provide a new plant trait, to enhance an existing plant trait, or to otherwise modify expression of plant phenotypes exhibited by the plant. Such traits include herbicide resistance, pesticide resistance, disease resistance, environmental tolerance (e.g., heat, cold, drought, salinity), morphology, growth characteristics, nutritional content, taste yield, horticultural characteristics, consumer (quality) traits, and the like.

A functional gene to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenuous gene within the plant. It will be appreciated that control of gene expression can have a direct impact on the observable plant characteristics.

Often the functional genes to be introduced will be modified from their native form. For example, sense and anti-sense constructs referred to above often have all or a portion of the transcript of the native gene operably linked to a promoter sequence at the 5' end of the transcribable segment, and operably linked to the 3" sequence of another gene (including polyadenylation sequences) at the 3' end of the transcribable segment. As is apparent to those skilled in the art, the promoter sequence could be one of the many plant active sequences already described. Alternatively, other plant-active promoter sequences could be derived specifically to be linked to the transcribable segment. The promoter can be endogenous to a particular plant species, or can be from an exogenous source such as a cauliflower mosaic virus 35S promoter (Odell et al., Nature 313:810–812 (1985)), the ubiquitin 1 promoter, or the Smas promoter. The 3' end sequence to be added can be derived from another plant gene, or less preferably from any other eukaryotic gene.

The fact that a gene of interest is co-introduced with a selectable marker gene refers to the fact that the sequences are coupled to each other or otherwise introduced together in such a manner that the presence of the selectable marker gene in a cell indicates that the gene of interest has been introduced into the cell. The two nucleotide sequences are typically, although not necessarily, part of the same genetic construct and are introduced by the same vector. A genetic construct containing the two nucleotides sequences will typically, but not necessarily, contain regulatory sequences enabling expression of each nucleotide sequence for example, promoter and transcription terminators.

The term "cells" within the context of the present invention is intended to refer to any type of cells from which individual genetically transformed cells may be identified and isolated using the method of the invention, and includes cells of plants, animals and microorganisms such as bacteria, fungi, yeast, etc. Furthermore, the term cell is includes protoplasts. Particularly preferred cells are plant cells and bacteria. More particularly the transformed plant cells and plants, seeds or progeny derived therefrom include: fruits such as tomato, mango, peach, apple, pear, strawberry, banana and melon; field crops such as canola, sunflower, tobacco, soybean and sugar beet; small grain cereals such as wheat, barley, rice, corn, and cotton; ornamentals; forages such as alfalfa, clover, forage grasses; forest trees; and vegetables crops such as potato, carrot, lettuce, cabbage and onion. Most preferably are soybean and corn.

The term "population of cells" refers to any group of cells which has be subjected to genetic transformation. The population may be a tissue, an organ or a portion thereof, a population of individual cells in or on a substrate, for example, a culture of microorganism cells, or a whole organism, for example, an entire plant.

The term "selecting" refers to the process of identifying and/or isolating genetically transformed cells from the non-transformed cells in a population of cells using the methods disclosed herein.

The gene of interest and the selectable marker gene may be introduced independently. The same bacteria may be used for incorporation of both genes and incorporating a relatively large number of copies of the gene of interest into the cells, whereby the probability is relatively high that cells which are shown to express the selectable marker gene also will contain and express the gene of interest. Independent introduction of two or more genes resulting in co-expression of the genes in the same cell is generally expected to have low probability, and the improved selection frequencies obtained by the positive selection method described herein are therefore expected to be especially advantageous in such systems.

The term "marker compound" as used herein may be any compound or nutrient in inactive or precursor form which in the absence of, for example, expression of the selectable marker gene exists in a form which is substantially biologically inactive with respect to the cells in question, but which when the selectable marker gene is expressed or transcribed is hydrolyzed or otherwise activated or metabolized so as to provide the genetically transformed cells containing the gene of interest with a selective advantage, and thereby allowing the cells to be selected. Preferred compounds include, but are not limited to, arabitol or ribitol and derivatives or precursors thereof, and alternatively mannitol and derivatives and precursors thereof. A "derivative" of arabitol or ribitol refers to any compounds capable of being utilized by, binding to, being a substrate for, or a product of any protein involved, either directly or indirectly, in the metabolism of arabitol or ribitol.

The marker compound used in the invention need not be one which is activated directly by a polypeptide encoded by the selectable marker gene. It may be activated indirectly, for example whereby the selectable marker gene has an indirect effect upon the marker compound in genetically transformed cells but not in non-transformed cells. Thus, the selectable marker gene may be one which upon expression in the transformed cells, for example, indirectly increases the activity of an enzyme which is endogenous to the population of cells, thereby leading to a greater enzyme activity and activation of the compound in question in the genetically transformed cells.

The term "selective advantage" as used herein includes the terms selective, metabolic and physiological advantage and means that the transformed cells are able to grow more quickly than disadvantaged (non-transformed) cells, or are advantageously able to utilize substrates (such as nutrient precursors, etc.) which disadvantaged cells are not able to utilize, or are able to detoxify substrates which are toxic or otherwise growth inhibitory to disadvantaged cells or a combination thereof. However, the non-transformed cells do not necessarily suffer any severe disadvantage in the sense of being damaged or killed or as is the case with negative selection using antibiotics or herbicides.

Therefore the positive selection as used in the context of the present invention refers to the use of a selectable marker gene which produces or increases a positive effect of an added compound on the transformed cells.

A protein which is "involved in the metabolism of a marker compound" is typically, but not exclusively, an enzyme which may be responsible directly or indirectly for the production or utilization of the marker compound or its derivatives or precursors. The protein may also be involved in the metabolism of a marker compound if it binds to it, transfers it from one site to another within or transport into the cell or tissue or organism or otherwise sequesters it thereby altering its local availability.

A region of nucleotide sequence which "regulates the activity of a gene encoding a protein" may alter the level of expression of an endogenous gene by being a promoter, or having a promoter activity therefor, and by being introduced in or near its vicinity. By "near" is meant up to 10,000 kb. Alternatively, indirect regulation may arise by altering the binding of RNA polymerase to the promoter of a structural gene encoding a protein, or complementary binding of the nucleotide sequence to at least a part of the structural gene, thus typically reducing the quantity of the protein in the cell.

Use of the present positive selection method in vivo is of particular relevance, for example, in connection with transformation performed on whole plants or on plant parts, in which the plants or parts comprise both transformed and non-transformed cells, since selection of the transformed cells is achieved without directly damaging the neighboring non-transformed cells. The transformed cells thus have a selective "advantage" compared to the non-transformed cells (e.g. the ability to thrive and grow; in plants, e.g., the ability to form shoots, etc.), but the non-transformed cells do not suffer any severe disadvantage in the sense of being damaged or killed, as in the case with negative selection using antibiotics or herbicides.

The selective advantage possessed by the transformed cells may typically be a difference or advantage allowing the transformed cells to be identified by simple visual means, i.e. without the use of a separate assay to determine the presence of a marker gene.

A population of cells may be cultivated on or in a medium containing at least one compound which may be inactive and which is directly or indirectly activated in the transformed cells, the compound being inactive in non-transformed cells or less active in non-transformed cells than in transformed cells, such that the transformed cells are provided with a selective advantage allowing them to be selected from the cell population.

The population of cells may also be cultivated on or in a medium containing a compound which is made available for the transformed cells by expression or transcription of the nucleotide sequence, the compound not being available for the non-transformed cells or being less available for non-transformed cells, such that the transformed cells are provided with a selective advantage.

The cells may also be transformed with a selectable marker gene which may encode a permease or other transport factor which allows the marker compound to cross the cell membrane and enter the transformed cells or to cross another (organelle) membrane, so that "activation" of an inactive compound involves selective uptake of the compound by transformed cells, and uptake by non-transformed cells is not possible or takes place to a lesser extent. Instead of facilitating uptake of a compound into the cell, the positive selection gene may alternatively direct its product to a compartment in which the inactive compound is located, for example, outside the plasma membrane or into the vacuole or the endoplasmic reticulum.

A compound used for selection purposes may in addition have both a positive and a negative effect. For example, certain carbon sources in sufficiently high concentrations can be toxic to most plants, but in cells containing arabitol or ribitol metabolizing enzymes, the negative effect is eliminated and the cells further obtain the benefit of being able to use these compounds as a carbohydrate source. In this case a single compound and a single or group genes together provide a combined positive and negative selection system, although such a system may also be established using two or more genes which together are responsible for inhibition of the negative effects of a compound and manifestation of the positive effects of the compound in the transformed cells.

The cells may be transformed with any nucleotide sequence which it is desired to incorporate therein to. Such a nucleotide sequence may encode genes providing for viral, fungal, bacterial or nematode resistance.

The protein encoded by the gene of interest or preferably the selectable marker gene is preferably an enzyme involved in arabitol or ribitol metabolism. Such enzymes include ribitol or D-arabitol dehydrogenease, ribitol or D-arabitol kinase, or D-ribitol or D-arabitol transporter gene. Scangos and Reiner, *Journal of Bacteriology*, 134:492–500 (1978).

Examples of compounds which can exert a physiological effect upon entering the cell, but which are not easily taken up into the cell or a cell compartment, are strongly hydrophilic or hydrophobic compounds, in particular charged compounds, large molecules such as polymers, in particular proteins, peptides, oligo- and polysaccharides, including plant hormones, phosphorylated metabolites such as phosphorylated carbohydrates, phosphorylated vitamins, phosphorylated nucleosides, including cytokinins, and compounds which are conjugated to carboxylic acid-containing carbohydrates or amino acids, including plant hormone conjugates.

Also, it is contemplated that the basic method of the present invention may be modified so that, instead of activating an inactive compound or nutrient in the transformed cells, selection may be performed by blocking the metabolism or synthesis of a compound in these cells.

When a polypeptide encoded by the selectable marker gene or the gene of interest directly activates an inactive compound or nutrient in the transformed cells, the non-transformed cells may in certain cases contain or produce a certain amount of the polypeptide in question. For example, when the activating polypeptide is an enzyme, the non-transformed cells may contain a certain native enzyme activity, the native enzyme being of the same type as the introduced activating enzyme. In such cases the "inactive compound or nutrient" need not necessarily be completely inactive in the non-transformed cells, since it may be sufficient that the compound or nutrient is merely substantially less active in non-transformed cells than in transformed cells. In other words, a qualitative difference between the transformed cells and the non-transformed cells with regard to activation of the initially inactive compound or nutrient may in certain cases be sufficient for selection purposes. In such cases inhibitors or substrates which compete with the native enzymes may be added. Especially suitable are inhibitors activated by the native enzyme, resulting in self-catalyzed production of the active inhibitor to a level at which the native enzyme is substantially totally inhibited.

The various methods employed in the preparation of the plasmids and transformation of host organisms are well known in the art and are described, for example, in U.S. Pat. Nos. 5,011,909 and 5,130,253. These patents are incorporated herein by reference. These procedures are also described in Sambrook et al., *Molecular Cloning: A Laboratory Manual*, Cold Spring Harbor Laboratory Press, Cold Spring Harbor, N.Y. (1989). Methods of transformation for use in accord with the subject invention can include those conventional to the art, such as use of Agrobacterium, viral vectors, microinjection, PEG, biolistics, and electroporation which are all routinely used to introduce foreign DNA into plant cells. The mode of transformation is not necessarily critical to the subject methods. Those skilled in the art will appreciate that as other transformation methods are developed, these new transformation methods can be practiced in accord with the teachings herein. Once in the cell, the foreign DNA is incorporated into the plant genome. In a particular embodiment, the transformation contemplates constructing a vector comprising a gene of interest and a selectable marker gene, placing the vector into a selected strain of Agrobacterium, and treating selected plant cells with the *Agrobacterium* under conditions sufficient to result in transfer of at least some of the vectors from the Agrobacterium to the plant cells, whereby the polynucleotide is expressed in the plant cells. Regulatory sequences can include both promoter and termination sequences.

Possible regulatory sequences can include, but are not limited to, any promoter already shown to be constitutive for expression, such as those of viral origin (CaMV 19S and 35S, TMV, AMV) or so-called "housekeeping" genes (ubiquitin, actin, tubulin) with their corresponding termination/poly A+sequences. Also, seed-and/or developmentally-specific promoters, such as those from plant fatty acid/lipid biosynthesis genes (ACPs, acyltransferases, desaturases, lipid transfer protein genes) or from storage protein genes (zein, napin, cruciferin, conglycinin, or lectin genes, for example), with their corresponding termination/poly A+sequences can be used for targeted expression. In addition, the gene can be placed under the regulation of inducible promoters and their termination sequences so that gene expression is induced by light (rbcS-3A, cab-1), heat (hsp gene promoters) or wounding (mannopine, HGPGs). It is clear to one skilled in the art that a promoter may be used either in native or truncated form, and may be paired with its own or a heterologous termination/polyA+sequence.

Plant tissue for use in transformation may be obtained from any suitable plant, i.e., known to be susceptible to transformation by known methods. Appropriate plant tissue includes, but is not limited to, leaves, hypocotyls, cotyledons, stems, callus, single cells, and protoplasts.

In a particular embodiment, transformed callus tissue is selected by growth on selection medium (e.g., medium which contains carbon source only utilizable by transformed plant cells). Transformed plants are regenerated and screened for the presence of the gene of interest. This involves analyzing tissue by at least one molecular or biological assays to determine which, if any, transformants contained the gene of interest. These assays include assays or observation of the tissue for growth, and assays of the tissue for the presence of gene of interest by, for example, a Southern assay or a PCR assay.

Those plants which are positive for the gene of interest are grown to maturity, and tissue can be analyzed for the expression of the gene of interest by looking for the polypeptide encoded by the polynucleotide, as for example via a Western blot analysis, and for the phenotype conferred to the plant by the gene of interest.

It is now well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a plant cell can be calculated by averaging frequency of preferred codon usage in a large number of genes expressed by the plant cell. It is preferable that this analysis be limited to genes that are highly expressed by the host cell.

Thus, in one embodiment of the subject invention, plant cells can be genetically engineered, e.g., transformed with genetic contructs to attain desired expression levels of the gene of interest. To provide genes having enhanced expression, the DNA sequence of the gene of interest can be modified to comprise codons preferred by highly expressed genes to attain an A+T content in nucleotide base composition which is substantially that found in the transformed host cell. It is also preferable to form an initiation sequence optimal for said plant cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the plant cell to specify that amino acid. As is appreciated by those skilled in the art, the distribution frequency of codon usage utilized in the synthetic gene is a determinant of the level of expression.

In a preferred embodiment, the selectable marker genes pertain to SEQ ID NO.: 1 and SEQ ID NO.:2 as well as fragments or functional mutants thereof that are capable of metabolizing a marker compound to confer a selective advantage. Such fragments and mutants will be readily obtainable following the teachings herein coupled with the state of the art. For example, using specifically exemplified polynucleotides as probes, useful polynucleotides can be obtained under conditions of appropriate stringency. The present invention further relates to variants of the present polynucleotides which encode for fragments, analogs and derivatives of the polypeptides having the sequences shown in SEQ ID NO.: 3, SEQ ID NO.:4, and SEQ ID NO.:5. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied topolynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequences shown in SEQ ID NO.: 3, SEQ ID NO.:4, and SEQ ID NO.:5; variants, analogs, derivatives and fragments thereof.

Further particularly preferred in this regard are polynucleotides encoding one or more gene products of the ribitol or arabitol operons (e.g., RtlT, RtlK, RtlD, RtlR, AtlD proteins), or combinations thereof, and fragments, and variants, analogs and derivatives of the fragments, which have the amino acid sequences exemplified herein in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the proteins. Also especially preferred in this regard are conservative substitutions. Most highly preferred are polynucleotides encoding polypeptides shown in SEQ ID NO.: 3, SEQ ID NO.:4, and/or SEQ ID NO.:5 without substitutions.

Further preferred embodiments of the invention are polynucleotides that are greater than 79%, preferably at least 85%, more preferably at least 90% identical to a polynucleotide encoding SEQ ID NO.: 1 and SEQ ID NO.:2, and polynucleotides which are complementary to such polynucleotides. Among these particularly preferred polynucleotides, those with at least 90%, 95%, 98% or at least 99% identity are especially preferred.

Particularly preferred embodiments in this respect, moreover, are polynucleotides which encode polypeptides which retain substantially the same or even exhibit a reduction in the biological function or activity as the mature polypeptide encoded by the polynucleotides described above.

The present invention further relates to polynucleotides that hybridize to the herein above-described sequences. In this regard, the present invention especially relates to polynucleotides which hybridize under stringent conditions to the herein above-described polynucleotides. A preferred level of stringency is such that hybridization will only occur if there is at least 85%, and preferably still 90%, and more preferably 95%, and even more preferably 97% identity between the sequences. The terms "identity" and "similarity", as used herein, and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculate (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton is Press, New York, 1991). Methods commonly employed to determine identity or similarity between two sequences include, but are not limited to those disclosed in Carillo, H., and Lipman, D., SIAM J. Applied Math., 48:1073 (1988). Preferred methods to determine identity are designed to give the largest match between the two sequences tested. Methods to determine identity and similarity are codified in computer programs. Typical computer program methods to determine identity and similarity between two sequences include, GCG program package (Devereux, J., et al., Nucleic Acids Research 12(1):387 (1984)), BLASTP, BLASTN, FASTA and TFASTA (Atschul, S. F. et al., J. Mol. Biol. 215:403 (1990)).

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5M Na ion, typically about 0.01 to 1.0M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3. 0M NaCl/0.3M trisodium citrate) at 50 to 55° C. Exemplary moderate stringency conditions include hybridization in 40 to 45% formamide, 1M NaCl, 1% SDS at 37° C., and a wash in 0.5× to 1×SSC at 55 to 60° C. Exemplary high stringency conditions include hybridization in 50% formamide, 1M NaCl, 1% SDS at 37° C., and a wash in 0.1× SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, Anal. Biochem., 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 100° C. Generally, stringent conditions are selected to be about 5° C. lower than the thermal melting point ($T_m$) for the specific sequence and its complement at a defined ionic strength and pH.

However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$) Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology— Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

The teachings of all of the references cited throughout this specification are incorporated herein by this reference to the extent that they are not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 1

Transformation of E.Coli with rtl Operon and Growth on Ribitol Medium

Materials and Methods

Initial work was done with clones of the operon for ribitol metabolism (Rbt) from *Klebsiella pneumoniae*, supplied by S. Turgot, Universität Osanbrtück. From these, a ~7.2 kb BamHI fragment was obtained from pFCK1, which contains the entire Rbt operon, plus approximately 2.3 kb of sequences 3' from the operon. A ~6.51 kb HindIII-BamHI fragment was obtained from pLTH9, which lacks the first 720 bp from the repressor. Finally, a ~3.98 kb ClaI fragment was obtained from pLTH1, which lacks the repressor altogether, as well as any sequences 3' to the operon. All bacteria were grown at 37° C. and shaken at 275–300 rpm.

The *K. pneumoniae* fragments were released via enzymatic digestion as recommended by the manufacturer (NEB, Beverly, Mass.), and blunted into the StuI site of pMECA (Thomson and Parrott 1998). Following T4 DNA ligation with Fastlink ligase (Epicentre, Madison, Wis.), pMECA was transformed via electroporation into *E. coli* strain DH10B (Life Technologies, Gaithersburg, Md.) and placed in 2B minimal broth as recommended by BRL (Bethesda, Md.) supplemented with 2 g l$^{-1}$ of ribitol (=adonitol, Sigma, St. Louis), 50 mg l$^{-1}$ each of L-leucine and L-isoleucine, and 1 mg l$^{-1}$ thiamine. The inorganic components of 2B medium are in Table 1. All organic components were filter-sterilized. Only successful cloning events of rbt were expected to result in bacterial growth, and successful growth demonstrated that ribitol could be used to maintain a high-copy plasmid in an *E. coli* K-12 strain.

Figure 1:
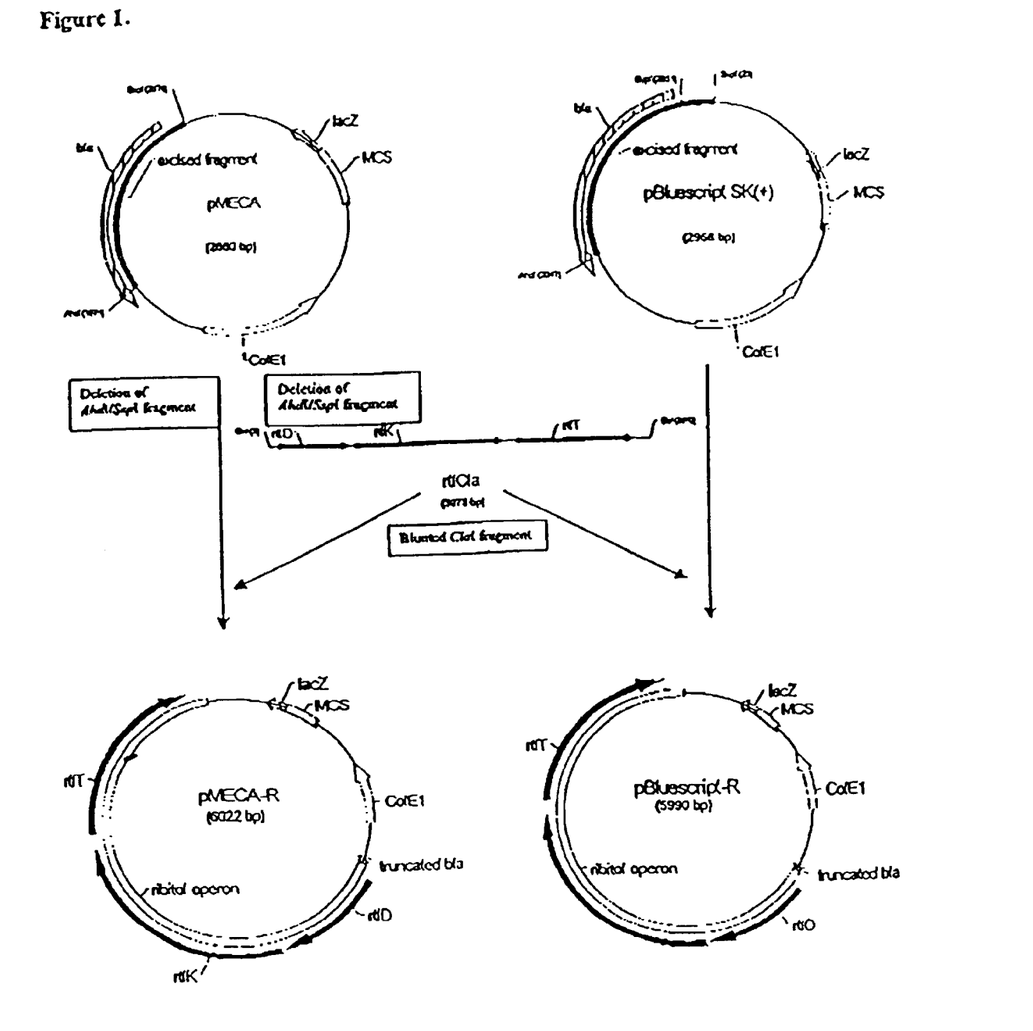
FIG. 1 shows a schematic of the isolation and cloning of the *E. coli* rtl operon.

Next, the corresponding genes of the rtl operon were isolated from *E. Coli* strain C, which was obtained as stock number 3121 from the *E. coli* Genetic Stock Center at Yale University, and grown in 2B minimal broth supplemented with 2 g $1^{-1}$ of ribitol. Total genomic DNA was isolated according to Syn and Swarup (2000). The genomic DNA was subject to digestion by ClaI. Following T4 DNA ligation into the corresponding site of pHEX3 (Heuel et al. 1997) and transformation into DH10B, incubation took place in 5 ml of 2B minimal broth supplemented as described previously. After 24 hours, 1 ml was placed in 25 ml of the same medium. As before, only successful cloning events could result in bacterial growth. Next, bacterial colonies were obtained following plating an aliquot of the liquid medium onto plates with solid LB medium supplemented with 20 mg $1^{-1}$ chloramphenicol. A single colony was grown in TB, and plasmid DNA isolated using a QuantumPrep kit (Biorad, Hercules, Calif.) and sequenced using a Model 377 automated DNA sequencer (PE Applied Biosystems, Forster City, Calif.) by the University of Georgia Molecular Genetics Instrumentation Facility. Sequence comparisons were made using the on-line BLAST programs of the National Center for Biotechnology Information (Bethesda, Md.), and the GAP program of the Wisconsin Package, ver. 10.1 (Genetics Computer Group, Madison, Wis.). To replace bla from pBluescript (Stratagene, La Jolla, Calif.) and pMECA with the rtl components, the ClaI fragment liberated with enzymatic digestion, blunt-ended, and isolated as a 4-kb fragment from a low melting point Seaplaque agarose gel (FMC Bioproducts, Rockland, Me.). The recipient plasmids were cut open with AhdI, blunted with T4 DNA polymerase and digested with SspI to remove nearly the entire sequence of the bla gene. The fragment was ligated into the plasmids usingT4 DNA ligase. These events are diagramed in FIG. 1. Ligated plasmids were transformed into DH10B and grown in 2B minimal broth supplemented with 2 g $1^{-1}$ of ribitol. For DH10B, the 2B medium was additionally supplemented with 50 mg $1^{-1}$ each of L-leucine and L-isoleucine, and 1 mg $1^{-1}$ thiamine. The resulting plasmids were named pMECA-R and pBluescript-R. Plasmid maps were drawn with Plasmid 1.1 (Redasoft, Toronto, Canada).

Growth rates and plasmid yields were compared for pMECA, pMECA-R, pBluescript, and pBluescript-R in DH10B. Both pMECA and pBluescript were grown in LB broth and in 2B minimal broth supplemented with 2 g $1^{-1}$ glucose. pMECA-R and pBluescript-R were grown in 2B minimal broth supplemented as described above. Bacteria were inoculated into 2 ml of their respective media, allowed to grow for 17 or 41 hours, and plasmid DNA isolated as described previously. Plasmid yield was quantified with a DNA fluorometer (Hoefer Scientific, San Francisco, Calif.). Each treatment was repeated three times.

Plasmid yields were also quantified for pMECA-R and pBluescript-R containing an insert in their MCSs. A PstI/AscI fragment from pTFG containing the cauliflower mosaic virus 35S promoter-GUS-nos terminator construct out of pTRA140 (Zheng et al. 1991) was ligated into the PstI and AscI sites of pMECA-R and a PstI-StuI fragment of pTFG into the PstI and EcoRV sites of pBluescript-R. The ligated plasmids were transformed into DH10B, cultured, isolated, and quantified as described above.

Results and Discussion

The ribitol operon from *E. coli* C contains 4 genes, in order as follows: rtlR, rtlD, rtlK, and rtlT. The first is a repressor, and contains the promoter for the operon. RtlD codes for NAD-dependent ribose dehydrogenase which converts ribose to D-ribulose. RtlK codes for ATP-dependent ribulose kinase, which converts D-ribulose to D-ribulose-5-phosphate, and which can be metabolized by all *E. coli* strains. Finally, rtlT codes for a ribose-specific ion symporter protein (Heuel et al. 1998).

Though the BamHI, ClaI, and HindIII-BamHI rbt fragments all conferred the ability to grow on ribitol, the ClaI fragment, which completely lacks the repressor, was all that was required for growth on ribitol, so subsequent work did not attempt to include rtlR in the cloning work. The sequence of this ClaI fragment has been deposited in GenBank, Accession No. AY005817. The ribitol operons of Klebsiella and Escherichia are thought to have a common evolutionary origin, and Heuel et al. (1998) reported 82% base identity between rbt and rtl based on partial sequencing. A BLAST comparison using complete sequences between the K, D, and T components of rbt and rtl, while revealing highly conserved regions, found greater homology at the amino acid level than the DNA level. The base pair identity for the rbt and rtl ClaI fragments was 70%. Amino acid identity was 87, 70, and 83% between the rbt and rtl dehydrogenase, kinase, and transporter components, respectively. When substitution with similar amino acids is considered, the homologies rise to 94, 79, and 89%, respectively.

The bla gene is only 788 bp long, in contrast to rtlK, rtlD, and rtlT, which are collectively 3971 bp long. We were able to compensate to some extent for the size difference by eliminating some of the DNA flanking the bla gene. Nevertheless, pMECA-R is 31683 bp larger than pMECA, and pBluescript-R is 3032 bp larger than pBluescript. Replacing bla with rtlD, rtlK, and rtlT inevitably brought along enzyme sites which led to the loss of uniqueness of enzyme sites within the pMECA and pBluescript MCSs. Nevertheless, pMECA-R still has 30 unique sites, while pBluescript-R has 18 unique sites. These are listed in Table 2.

Figure 2:
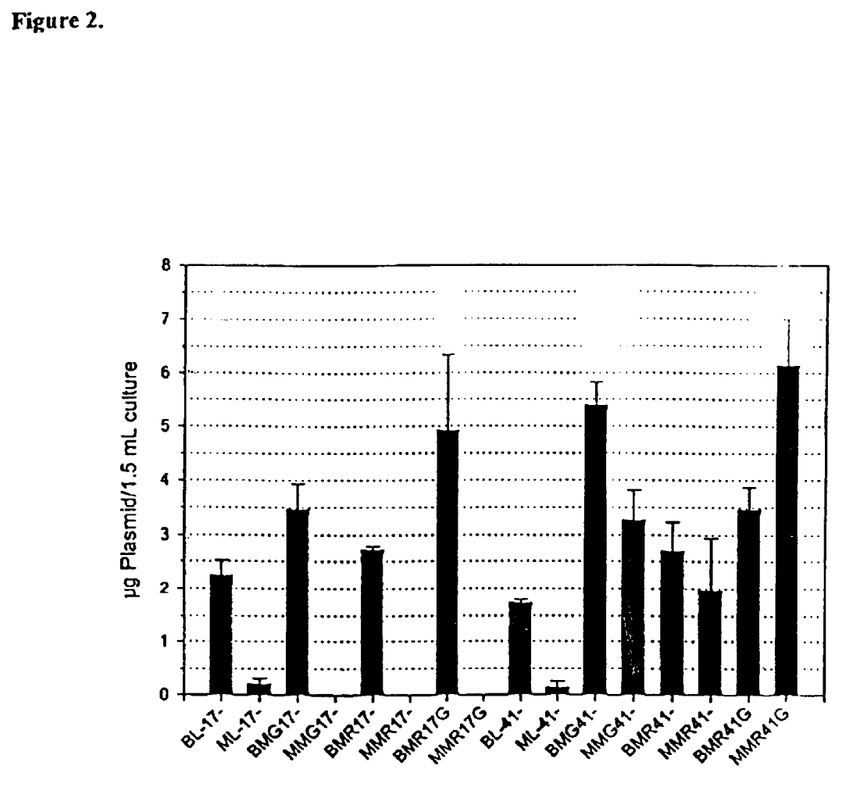
FIG. 2 shows a graph representing comparative plasmid yields in DH10B of pBluescript and pMECA, growing in LB broth or 2B broth minimal medium supplemented with glucose, and of their ribitol derivatives growing on 2B minimal medium with ribitol. Plasmid yield data were collected at 17 and 41 hours. Plasmid yields for pBluescript-R and pMECA-R with a GUS construct cloned into their multiple cloning sites were also compared. Bars represent the average of three replications +/− standard error. Legend: The first letter signifies the plasmid backbone: B=pBluescript, M=pMECA. The second letter indicates the medium:L=Luria-Bertani broth, M=2B minimal medium. The third position denotes the carbohydrate source: a '−' means no additional carbohydrate, G=glucose, and R=ribitol. The number is for the amount of growth time: 17 or 41 hours. The final position denotes if the plasmid had an insert cloned into its multiple cloning site: a '−' means no insert, and G refers to a GUS construct.

Plasmid yields for DH10B are depicted in FIG. 2. Heuel et al. (1998) reported that high-copy number plasmids containing dal or rbt were unstable under arabitol or ribitol selection, but we did not experience any such difficulties.

For the Bluescript plasmids, yields were higher in 2B minimal medium than in the standard LB broth. Yields of the ribitol version were essentially like those of the ampicillin version when grown in minimal medium. On a molar basis, yields in 2B minimal medium with ribitol are lower than those in 2B minimal medium with glucose, as the ribitol version of pBluescript is twice as large as the ampicillin version. Insertion of a GUS construct into the MCS did not significantly affect plasmid yield.

For the MECA plasmids, yields were negligible at the 17-h time point. When pMECA lacks an insert in its MCS, the growth rate of its host cells is slowed down, an effect that is particularly pronounced in strain DH10B. This slow-growth trait is useful to identify colonies containing inserts (Thomson and Parrott 1998). By 41 hours, growth of pMECA in 2B minimal medium was significantly greater than that in LB, although the ampicillin version outgrew the ribitol version. Yields for pMECA-R containing an insert were as high after 41 hours as those for pBluescript-R after 17 hours.

Ribitol selection should work with any K-12 strain of *E. coli*. The K-12 strains in use today have an absolute requirement for essential nutrients in the growth medium, as the parent strain has been subject to extensive mutagenesis since its isolation in 1922 (Bachmann 1972). Since different K-12 strains have different growth requirements, minimal growth medium must be adjusted for each K-12 strain by adding the necessary nutrients that each particular strain requires. p Finally, Reiner (1975) listed individual bacterial strains which have been identified based on their ability to metabolize either sucrose or raffinose. The cloning of these operons should permit the development of additional vectors which would permit the use of these carbohydrates in a selection system, either for the maintenance of plasmids in bacteria, or for the selection and recovery of transgenic plants.

References

Bachmann B J (1972) Pedigrees of some mutant strains of *Escherichia coli* K-12. Bacteriol Rev 36:525–557

Heuel H, Shakeri-Garakani A, Turgut S, Lengeler J W (1998) Genes for D-arabinitol and ribitol catabolism from *Klebsiella pneumoniae*. Microbiology 144:1631–1639

Heuel H, Turgut S, Schmid K, Lengeler J W (1997) Substrate recognition domains as revealed by active hybrids between the D-arabitol and ribitol transporters from *Klebsiella pneumoniae*. J Bacteriol 179:6014–6019

Klein T M, Wolf E D, Wu R, Sanford J C (1987) High-velocity microprojectiles for delivering nucleic acids into living cells. Nature 327:70–73

NCTC (1983) Catalogue of the National Collection of Type Cultures, 6th Edition. Public Health Laboratory Service, London Reiner A M (1975) Genes for ribitol and D-arabitol catabolism in *Escherichia coli*: their loci in C strains and absence in K-12 and B strains. J Bacteriol 123:530–536

Syn C K C, Swarup S (2000) A scalable protocol for the isolation of large-sized genomic DNA within an hour from several bacteria. Anal Biochem 278:86–90

Tartof K D, Hobbs C A (1987) Improved media for growing plasmid and cosmid clones. Focus 9:12–16

Thomson J M, Parrott W A (1998) pMECA: A cloning plasmid with 44 unique restriction sites that allows selection of recombinants based on colony size. BioTechniques 24:922–927.

Wiman M, Bertani G, Kelly B, Sasaki I (1970) Genetic map of *Escherichia coli* strain C. Mol Gen Genet 107:1–31

Zheng Z, Hayashimoto A, Li Z, Murai N (1991) Hygromycin resistance gene cassettes for vector construction and selection of transformed rice plants. Plant Physiol 97:832–835

EXAMPLE 2

Isolation and Sequencing of Arabitol Dehydrogenase

Total genomic DNA was isolated from *E. coli* strain C, digested with PstI, the resulting fragments were ligated into pBluescript, and transformed into *E. coli* DH10B. The *E. coli* was then grown on 2B Minimal Medium as described by LaFayette and Parrott (2001; A non antibiotic marker for amplification of plant transformation vectors in *E. coli*. Plant Cell Rep, In press), except that arabitol was substituted for ribitol.

One colony able to grow on arabitol was isolated, and the plasmid purified from it was digested with PstI, releasing 3 fragments. Individually subcloning the larger fragments into pBluescript did not give the ability to grow on arabitol to the *E. coli* host. Hence, the correct fragment was identified by using the universal primer sites on pBluescript to amplify the insert and sequence its ends. One of the sequenced ends was homologous to the *Klebsiella pneumoniae* arabitol transporter. Evidently, the PstI cleaved the *E. coli* transporter, and without an intact transporter, *E. coli* cannot grow on arabitol.

Once the correct fragment was identified, the EZ::TN Insertion Kit from Epicentre Technologies was used. Primer sites on the TN transposon were used to determine which colonies had inserts in the arabitol operon, and which had them in the vector sequence. Plasmid was isolated from four colonies with transposon insertions in the arabitol operon, and the primer sites on the transposon used to amplify the insert fragments. These were sent for sequencing at the University of Georgia's Molecular Genetics Instrumentation Facility. The resulting sequences were assembled using BLAST to align the regions homologous to the enzyme counterparts in *P. klebsiella*. The sequence was determined to be the arabitol dehydrogenase gene (SEQ ID NO. 1). The second DNA strand was sequenced, and the resulting sequence was used to verify the sequence of the first strand.

Because plants have the ability to grow on D-xylulose (Haldrup, et al., 1998), transformation of plants with atlD confers the ability to grow in a medium containing arabitol. We have confirmed that soybean embryos are capable of growing on fructose. See also Linn 1996. Accordingly, because atlD confers the ability to convert mannitol to fructose (Viola, 1996; Kanabus, et al., 1986), transformation of plants with atlD should also confer the ability to grow in a medium containing mannitol.

References

Haldrup, A., Petersen, S. & Okkels, F. (1998) Positive selection: A plant selection principle based on xylose isomerase, an enzyme used in the food industry. Plant Cell Rep. 18, 76–81.

Kanabus, J., Bressan, R. & Carpita, N. (1986) Carbon assimilation in carrot cells in liquid culture. Physiol. Plant. 82, 363–368.

Linn, E. (1961) An inducible D-arabitol dehydrogenase from *Aerobacter aerogenes*. J. Biol. Chem. 236,31–36.

Viola, R. (1996) Hexose metabolism in discs excised from developing potato (*Solanum tuberosum* L.) tubers. II. Estimations of fluxes in vivo and evidence that fructokinase catalyses a near rate-limiting reaction. Planta 198, 186–196.

EXAMPLE 3

Transformation of Plant cells rbt or dal Operon

Somatic embryos of Jack, a *Glycine max* (L.) Merrill cultivar with high embryogenic capacity, are induced from immature cotyledons, proliferated and maintained. See, as described by, Samoylov et al., Plant Cell Rep 18:49–54; Bailey et al., In Vitro-Plant. 29P: 102–108 (1993); and Bailey et al., Plant Sci. 93:117–120 (1993). Approximately 90 d after induction and 1 week after liquid suspensions are subcultured, clumps of globular-stage embryos are bombarded. The average clump diameter is 2 mm. Plasmid DNA produced by the procedures in Examples 1 and/or 2 is isolated using an alkalinelysis/ PEGpurification procedure (Yeung and Lau, *Biotechniques*. 15(3):381–2 (1993)), and is preferably coupled with a known promoter according to standard protocols. Plasmid DNA is suspended at equimolar amounts in a final concentration of 1 µg/L and precipitated onto 1-µm gold particles according to conventional protocols (see, e.g., Christou et al., *Plant Physiology* 87:671–674 (1988). The Bio-Rad PDS 1000H is used for bombardment. Each plate is bombarded twice using 650-psi rupture discs supplied by Bio-Rad in a 700-mm mercury vacuum. First, embryos are transferred to an open Petri dish and desiccated for 15 min and then mashed gently with a spatula. Ten plates of somatic embryos (1 g per plate) are bombarded. Following bombardment, embryos are dried for 30 min in a covered Petri dish. The embryos are subsequently transferred to MSD20 medium (Bailey et al., 1993, supra). Alternatively, Agrobacterium harboring a vector containing SEQ ID NO 1 or nucleotide sequences encoding the polypeptides shown in SEQ ID NOS: 3, 4, and/or 5 are used to transfer shoot segments according to standard protocols.

EXAMPLE 4

Selection of Transgenic Plant Cells using Arabitol or Ribitol as Selectable Markers and Plant Regeneration The clumps in each plate as describe in Example 3, the day after bombardment, are divided and transferred onto two selection plates containing MSD20 medium containing arabitol, ribitol, or mannitol (0–25 g/L). Preferably, the arabitol, ribitol, mannitol is provided in equimolar amounts with the sucrose in the MSD20 medium. Transfers to fresh medium are made every 3 weeks.

At week 6, surviving embryonic clusters are transferred to liquid FN medium (Samoylov et al., In Vitro Cell Dev.Biol.-Plant 34:8–13 (1998)). At this point putative transgenic cell lines are separated and tracked. Cells are allowed to acclimate for 4 weeks with a transfer to fresh medium after 2 weeks. Then, the clusters are transferred to FN containing arabitol or ribitol (0–25 g/L) for 2 weeks of final selection. The transgenic somatic embryos are germinated and converted using previously published methods (Bailey et al., 1993, supra). The $T_0$ plants are grown in 4-L pots in a sand: loam:bark mixture (1:1:1, w/w Hyponex Maryville, Ohio) under 23-h photoperiods (for vegetative growth) for 2 months in a glass greenhouse. Flowers are induced using 12-h photoperiods for the duration of the plants' life cycle. The $T_1$ plants are grown under similar conditions.

TABLE 1

Composition of 2B minimal medium. The final medium contains 100 ml of 2B stock I, 50 ml of 2B stock II, and 20 ml of 2B stock III per liter.

| Stock | Component | Amount per 100 mL |
| --- | --- | --- |
| 2B Stock I | $NH_4Cl$ | 2 g |
|  | $KH_2PO_4$ | 6 g |
|  | $Na_2HPO_4$ | 12 g |
| 2B Stock II | $MgSO_4.7H_2O$ | 0.26 g |
| 2B Stock III | $CaCl_2.2H_2O$ | 0.10 g |

TABLE 2

Unique enzyme sites in the multiple cloning sites of pMECA-R and pBluescript-R

| pMECA-R | pBluescript-R |
| --- | --- |
| EcoRI | SacI |
| EcoRV | NotI |
| SpeI | EagI |
| NotI | XbaI |
| Acc651 | SpeI |
| KpnI | SmaI |
| XhoI | PstI |
| BssHII | EcoRI |
| AscI | EcoRV |
| XbaI | HindIII |
| SfiI | HincII |
| Bsp120I | AccI |
| ApaI | SalI |
| PacI | XhoI |
| PmeI | ApaI |
| SalI | EcoO109I |
| AccI | DraII |
| XmaI | KpnI |
| SmaI |  |
| SrfI |  |
| PstI |  |
| SphI |  |
| NaeI |  |
| FseI |  |
| AvrII |  |
| HpaI |  |
| HindIII |  |
| NgoMIV |  |
| NheI |  |
| SwaI |  |

What is claimed is:

1. An isolated polynucleotide molecule comprising at least one gene of interest, and at least one selectable marker gene, wherein said at least one selectable marker gene comprises a nucleotide sequence which selectively hybridizes under high stringency conditions to the complement of a nucleotide sequence shown in SEQ ID NO: 2, or a plant optimized version thereof, wherein said nucleotide sequence encodes for a protein possessing ribitol dehydrogenase enzymatic activity and a protein possessing ribitol kinase enzymatic activity.

2. The Transgenic cells transformed with the polynucleotide molecule of claim 1, wherein the selectable marker gene gives said cells a selective advantage when a population of cells including the transformed cells and nontransformed cells is supplied with a marker compound.

3. The transgenic cells of claim 2 wherein said marker compound is arabitol, ribitol, or mannitol.

4. The transgenic cells of claim 2, wherein said transgenic cells comprise bacteria, fungi, yeast, plant or a combination thereof, and wherein said nucleotide sequence is optimized for expression in said cells.

5. A Plant or plant tissue regenerated from the cells of claim 2.

6. A method of selecting transformed cells from a population of cells comprising a) introducing into the genome of a cell a gene of interest and a selectable marker gene;

b) obtaining transformed cells;

c) supplying to the population of cells a marker compound wherein said transformed cells have a selective advantage over non-transformed cells due to expression or transcription of the the selectable marker gene in the presence of the marker compound; and d) selecting said transformed cells from the population of cells;

wherein said selectable marker gene comprises a nucleotide sequence which selectively hybridizes under high stringency conditions to the complement of a nucleotide sequence shown in SEQ ID NO: 2, or a plant optimized version thereof, wherein said nucleotide sequence encodes a protein that possesses ribitol dehydrogenase enzymatic activity and a protein that possesses ribitol kinase enzymatic activity;

and said marker compound comprises arabitol, ribitol, or mannitol.

7. The method of claim 6, wherein said cells comprise bacteria, fungi, yeast, plant or a combination thereof, and wherein said nucleotide sequence optimized for expression in said cells.

8. The method of claim 7, wherein said cells comprise plant cells.

9. Transformed cells selected according to the method of claim 6.

10. Transformed plants derived from the cells of claim 9.

11. Seeds produced from the transformed plants of claim 10, wherein said seeds are capable of germinating to produce transformed plants.

12. An isolated polynucleotide molecule comprising a nucleotide sequence which selectively hybridizes under high stringency conditions to the complement of a plant optimized version of the nucleotide sequences shown in SEQ ID NO: 2, and wherein said nucleotide sequence encodes for a protein possessing ribitol dehydrogenase activity and a protein possessing ribitol kinase activity.

13. An isolated polynucleotide molecule comprising at least one gene of interest, and at least one selectable marker gene, wherein said at least one selectable marker gene comprises a nucleotide sequence encoding SEQ ID NOS.: 3 and 4.

14. An isolated polynucleotide molecule comprising at least one gene of interest, and at least one selectable marker gene, wherein said at least one selectable marker gene comprises a nucleotide sequence which selectively hybridizes under high stringency conditions to the complement of a nucleotide sequence shown in SEQ ID NO: 1, or a plant optimized version thereof, wherein said at least one selectable marker gene encodes for a protein possessing arabitol dehydrogenase enzymatic activity.

15. A method of selecting transformed cells from a population of cells comprising
a) introducing into the genome of a cell a gene of interest and a selectable marker gene;
b) obtaining transformed cells;
c) supplying to the population of cells a marker compound wherein said transformed cells have a selective advantage over non-transformed cells due to expression or transcription of the selectable marker gene in the presence of the marker compound; and
d) selecting said transformed cells from the population of cells;
wherein said selectable marker gene comprises a nucleotide sequence which selectively hybridizes under high stringency conditions to the complement of a nucleotide sequence shown in SEQ ID NO: 1, or a plant optimized version thereof, and encodes a protein having arabitol dehydrogenase enzymatic activity;
and wherein said marker compound is arabitol.

16. A method of selecting transformed cells from a population of cells comprising
a) introducing into the genome of a cell a gene of interest and a selectable marker gene;
b) obtaining transformed cells;
c) supplying to the population of cells a marker compound wherein said transformed cells have a selective advantage over non-transformed cells due to expression or transcription of the selectable marker gene in the presence of the marker compound; and
d) selecting said transformed cells from the population of cells;
wherein said selectable marker gene comprises a nucleotide sequence encoding SEQ ID NO.: 3, and a nucleotide sequence encoding SEQ ID NO.: 4;
and wherein said marker compound is ribitol.

17. The method of claim 16, wherein said selectable marker gene further comprises a nucleotide sequence encoding SEQ ID NO.: 5.

18. The isolated polynucleotide molecule of claim 1, wherein said nucleotide sequence further encodes a protein possessing ribitol transporter activity.

19. The isolated polynucleotide molecule of claim 1, wherein codons of the nucleotide sequence that hybridizes to the complement of the nucleotide sequence of SEQ ID NO: 2 are substituted with plant preferred codons.

20. The method of claim 6, wherein codons of the nucleotide sequence that hybridizes to the complement of the nucleotide sequence of SEQ ID NO: 2 are substituted with plant preferred codons.

21. The isolated polynucleotide molecule of claim 12, wherein codons of the nucleotide sequence that hybridizes to the complement of the nucleotide sequence of SEQ ID NO: 2 are substituted with plant preferred codons.

22. The isolated polynucleotide molecule of claim 14, wherein codons of the nucleotide sequence that hybridizes to the complement of the nucleotide sequence of SEQ ID NO: 1 are substituted with plant preferred codons.

23. The method of claim 15, wherein codons of the nucleotide sequence that hybridizes to the complement of the nucleotide sequence of SEQ ID NO: 1 are substituted with plant preferred codons.

* * * * *

SEQUENCE LISTING

<160> NUMBER OF SEQ ID NOS: 5

<210> SEQ ID NO 1
<211> LENGTH: 1848
<212> TYPE: DNA
<213> ORGANISM: Escherichia coli

<400> SEQUENCE: 1

```
atgaacgaac aatttacatg gctgcacatc gggttaggtt cttttcatcg cgcacatcag      60
gcgtggtatc tacaccgttt gcaggtgatg ggcgataaac gctggagcat tgctgcgggc     120
aatattcgta atgatgctga acatgtcgta caggcactca gtgcacagaa aggtcgctat     180
gtgctggaaa ccgtcagccc ggaaggggta agcgaatatg aagagatcac ctcaattcag     240
aagttgatac cgtggcaggc agatttacaa ccgctgattg ctgaagggc  agatccgaag     300 acaaaagtga ttgctttcac cgtcaccgaa ggcgggtact acctgaatac cagtcacaaa     360
ctggaagtta acaatcctga tttagcggca gatcttaaag ggggatgcaa aacaatttac     420
ggtgttatta cccgtatcct cgaagcgcgt atggcaaata acgccggacc actaaccctg     480
atgaacgaac aatttacatg gctgcacatc gggttaggtt cttttcatcg cgcacatcag     540
gcgtggtatc tacaccgttt gcaggtgatg ggcgataaac gctggagcat tgctgcgggc     600
aatattcgta atgatgctga acatgtcgta caggcactca gtgcacagaa aggtcgctat     660
gtgctggaaa ccgtcagccc ggaagggta agcgaatatg aagagatcac ctcaattcag      720
aagttgatac cgtggcaggc agatttacaa ccgctgattg ctgaagggc  agatccgaag     780
```

-continued

```
acaaaagtga ttgctttcac cgtcaccgaa ggcgggtact acctgaatac cagtcacaaa       840
ctggaagtta acaatcctga tttagcggca gatcttaaag ggggatgcaa acaatttac        900 ggtgttatta cccgtatcct cgaagcgcgt atggcaaata cgccggacc actaaccctg        960 ctgaattgcg ataacgtgcg ccataatggt gaacgtttcc atgatggcct ggttgagttt      1020
ctccagctaa ctggcaaaca ggatgtcatc gactggctga gtacaaatac cacttgcccg      1080
aataccatgg ttgaccgcat tacgcctcgt ccggcagcag aacttccggc acggatcaag      1140
gctcaaacgg gtattgccga taaagcgccg gtaatgggcg aaacctttat ccagtgggtc      1200
gtggaagata atttccgtga tgtccgtccg gcactggaga aggtcggtgt cgaactggtg      1260
gcgtcggtaa tccectatga agaggcgaag attcgcattc ttaactcttc acacagttgc      1320
atcgcctggg caggtacgtt aatcggtcaa aaatatatcc acgaaagcac aatgaccgat      1380
tttatctatc agattgccga ccgctacgtg acggaagatg tcattccttg cttgggcgat      1440
aacggtatcg atttgccaac ctaccgtgat gttgtactca agcgttttac caatccacat      1500
attcaggaca ccaaccaacg cgtcgctgcg gatggttct cgaaaattcc ggcgatgatt       1560 gccccccacac tgcgagagtg ctaccagcga ggcgttcgcc cgaatgccac cgccatgtta    1620
cctgcactgt tttacgtatt catggagcag tggcatcacg gcaaactgcc ctatgaatat     1680
caggatggca tccttgatgc accagctgtc catgcaatgt acagtctgc cgatcccgtc      1740 gctgtttatg ccagtgataa agcgctgttt ggcgatttaa ccgaacgtga agattttgcc     1800
gcgttgttgc gcgaaaaaat cgctgacgtc tacgcgttaa ttaactaa                  1848

<210> SEQ ID NO 2
<211> LENGTH: 3971
<212> TYPE: DNA
<213> ORGANISM: Escherichia coli
<220> FEATURE:
<221> NAME/KEY: misc_feature
<222> LOCATION: (96)..(848)
<223> OTHER INFORMATION: ribitol dehydrogenase coding region
<220> FEATURE:
<221> NAME/KEY: misc_feature
<222> LOCATION: (859)..(2463)
<223> OTHER INFORMATION: ribitol kinase coding region
<220> FEATURE:
<221> NAME/KEY: misc_feature
<222> LOCATION: (2565)..(3839)
<223> OTHER INFORMATION: ribitol transporter coding region

<400> SEQUENCE: 2
atcgattgag cagtttgctt cacacggcag ctaaattccc gttcagtgcg tgcaagcaaa        60
cagagactat aaattcgccc tggtaaaagg attatatgat gaatcactct gtgccctcta      120
tgaatactcc ccttaatggc aaagttgcag ctatcactgg cgctgcgtca ggtattggcc      180
tgcaatgtgc aaaaacgctg ctcgatgcag gagcaaaggt agtattgatt gaccgggaag      240
gcgacaaact gcacaagatt gtcgctgagt taggcgaaaa cgcgtacgcg ctgcaactcg      300
atctcttcaa taatcagcaa gtcgataaca tgctggcgga cattatcgaa ctggcgggtg      360
ggctggatat ttttcatgcc aatgcaggcg cttatattgg cggcccagtg gctgaaggtg      420
atccagatgt ctgggatcgt gtgttaaatc tgaatataaa tgcggcgttt cgctgtgtcc      480
gtgcagtcct gccgcatatg attgcgcaga ggtcgggcga tataattttt accagttcca      540
tcgcgggcgt cgttccggtt atctgggaac cgatctacac cgcgtccaaa tttgccgttc      600
aggcattcgt acacactacc cgccgccagg tttctcaata tggcgtgcgt gtgggtgcgg      660
```

-continued

```
tgctgccagg accagtagtc actgccctgc ttgatgactg ccaaaagcc aaaatggaag      720 aagccctggc aaatggtagc ctgatgcaac cgattgaagt ggcggaatca gtattgttta      780
tggtgacccg ctcgaaaaat gtcaccgtgc gagatttagt gatcctgcct ggcagtgtcg      840
atctgtaagg gcgcaatcat gacaataacc aaaaccgtta ttggtgttga tgtgggatca      900
ggcagtgtcc gcgccgggat ttttgatctc aacggatctc tgctatccca tgccacagaa      960
aaaatcacga ctacgcggcg cagcggaagc gcgtggaac agtccagcca ggagatctgg      1020
caggcggtct gttcatgtat tcgtaatgcg ctcactctgg cagacgtttg tgcacaaagt      1080
gtggcaggca tcggttttga tgccacctgt tctctggtgg tactggataa aaacggtgat      1140
ccattgcctg tcagcccgga aggagatgca aagcaaaata tcattgtgtg gatggatcac      1200
cgcgccaccg aacaagcaga gcgaatcaat gccactcacc atccggtgct gaactacgtc      1260
ggtggtaaaa tttcgcctga atggaaaca ccgaaaattc tctggctgaa agaaaatatg      1320
ccagagatct acgaacgtgc cggacaattt ttcgatctgg ccgattttct gacctggcgg      1380
gctaccggtg atttagcgcg ttcagtatgc actgttacct gtaaatggac gtggctggca      1440
catgaaaatc gctgggatcc agattatttc cgcaccattg gccttgcaga gttagcggat      1500
gaagatttta ttcgcattgg tcatcatatt gtttctcccg aacaccttg tggaaatggt      1560 ttaacagcac aagccgcggc agagatggga ttactcccg gcacacctgt cgctgtaggg      1620
ttaattgatg ctcacgctgg tggcatcggt acggttggcg tagaaggtgg agcgctgaac      1680
aatctcgcgt atgttttcgg cacttcttca tgcaccatgg catctaccac ttctccctcg      1740
tttgtaccgg gtgtctgggg gccgtattac agtgcgatgg ttccaggtct gtggttagtt      1800
gaaggcggga aaagtgctgc gggagcagct attgaccagc tacttgattt ccatccggct      1860
gttgaagaag ctcgcgaaat ggcacaacgt gtgaatcagc ccctcccgt ctggcttgct      1920 gatcgaatcc tcgaaaaaac ggcgcaacca tcagatgctg tcgccctggc gaaagggcta      1980
cacgtggtgc cggaatttct cggaaatcgc gcccccttcg cagatcctca tgccagagcg      2040
gtaatttgtg gcctgggtat ggagcgagat ctggataatt tactcgcctt gtatatcgct      2100
ggattatgcg gaattggtta tggtctgcgc caaattctcg acgctcaaac agcgcaggga      2160
gtagtgagta aaaatatcgt tattagcggc ggtgccgggc agcatccact ggtacgacaa      2220
attctggcag ataccctgcgg tattccggtc attaccacgc aatgctgcga accggtttta      2280
ttaggctcgg ccattcttgg tgctgtcgcc ggaaatattg caccttctgt tggcgaagcg      2340
atgcaacaat tcacccatgt ggataaatat tattatccgc aagaacgcta tcaatctctt      2400
catcatcgtc gatatgaggc ctataagcag ttgcagcata ctgcaaaatt actcagagac      2460
taattaacca gccgcctgac gctgttttca ggcaatcact aataacgact cactccggta      2520
atatcccgga gtgcattcat ctgcacccta aaaacgaggt ttatatgtcc agaaataata      2580
aacagtggtt gggtttgcca ctgcatctga tatggggata tatcgccatc gcagtattta      2640
tgactggtga tggtttcgaa ctcgcattct tatcgcacta tattaaatcg ttaggcttca      2700
cacctgcgga agcctctttt gcctttacgc tctacgccct ggcggctgcc ctttccgcct      2760
gggtttctgg ggtagtagcg gaaatcatca cgccgcaaaa aaccatgctg attggttttg      2820
tcctatggtg cgtattccat gttctgtttc tggtctttgg attaggacag gcaaactatg      2880
ggttaatcct gctgttttac gggattcgtg gtttagcgta tccgctattt ctctactcat      2940
ttatcgtcgt tattattcat aacgtgcgta gcgaaaattc cagttctgct ctgggttggt      3000
actgggcggt atattcagta gggatcggtg ttgctggcag ttatattccc agttttacga      3060
```

-continued

```
taccgattat gggtgaaatg gaaccttat ggctggcact ggcgttctgc tttgctggcg      3120
gtgtcattgc catgatctcc ttgcgtcatg ttaaaacgcc tggacatatg cataatttaa      3180
ctccccgtga gaagtttgca gaattaagtc gggcagtaac tttactttat accaaccgca      3240
atatttttct ctccagtatt gtgcgcatta taaatacctt atcgttattc ggttttgcgg      3300
tcattatgcc aatgatgttt gtggatgaac tgggattcac cacctctgaa tggttgcagg      3360
tctgggcggc attttctttt accactattt tctctaatat ttttttggggg attgtggcag      3420 aaaaaatggg ctggatgcgt gttattcgct ggtttggttg cctcgggatg gcagcatcaa      3480
gtttagcgtt ttactacatg ccgcaatact ttggtcacaa ctactggatg caatgattc       3540 cggcgattgc tctgggaact tttgttgctg catttgtgcc gatggccgct gtcttcccgg      3600
cactggaacc aaaacacaaa ggtgctgcaa tctcggttta caacctctct gcgggtatgt      3660
ctaacttcct ggctccggca attgccgtgg tgttattacc gtggtttagc actatcggtg      3720
tggtcattgc ctatacagca ttgtatctat tggccttttgt cctttgcgca ttcattcgcg      3780
ttgagcagcc aggattcagt tctgcgccag tgactgagaa ggcattgaat atctcctgaa      3840
aaacgaaacg catcaggcac tcatcctctc cctcatggga gaggatgatt tcacatcagg      3900
caatagtgac tttgttatcg agataaacgt cctgcacggc gttaatcagt ttcacgccgt      3960
cagccatcga t                                                            3971
```

<210> SEQ ID NO 3
<211> LENGTH: 250
<212> TYPE: PRT
<213> ORGANISM: Escherichia coli

<400> SEQUENCE: 3

```
Met Met Asn His Ser Val Pro Ser Met Asn Thr Pro Leu Asn Gly Lys
1               5                   10                  15

Val Ala Ala Ile Thr Gly Ala Ala Ser Gly Ile Gly Leu Gln Cys Ala
                20                  25                  30

Lys Thr Leu Leu Asp Ala Gly Ala Lys Val Val Leu Ile Asp Arg Glu
            35                  40                  45

Gly Asp Lys Leu His Lys Ile Val Ala Glu Leu Gly Glu Asn Ala Tyr
        50                  55                  60

Ala Leu Gln Leu Asp Leu Phe Asn Asn Gln Gln Val Asp Asn Met Leu
65                  70                  75                  80

Ala Asp Ile Ile Glu Leu Ala Gly Gly Leu Asp Ile Phe His Ala Asn
                85                  90                  95

Ala Gly Ala Tyr Ile Gly Gly Pro Val Ala Glu Gly Asp Pro Asp Val
            100                 105                 110

Trp Asp Arg Val Leu Asn Leu Asn Ile Asn Ala Ala Phe Arg Cys Val
        115                 120                 125

Arg Ala Val Leu Pro His Met Ile Ala Gln Arg Ser Gly Asp Ile Ile
    130                 135                 140

Phe Thr Ser Ser Ile Ala Gly Val Val Pro Val Ile Trp Glu Pro Ile
145                 150                 155                 160

Tyr Thr Ala Ser Lys Phe Ala Val Gln Ala Phe Val His Thr Thr Arg
                165                 170                 175

Arg Gln Val Ser Gln Tyr Gly Val Arg Val Gly Ala Val Leu Pro Gly
            180                 185                 190

Pro Val Val Thr Ala Leu Leu Asp Asp Trp Pro Lys Ala Lys Met Glu
        195                 200                 205
```

```
Glu Ala Leu Ala Asn Gly Ser Leu Met Gln Pro Ile Glu Val Ala Glu
        210                 215                 220
Ser Val Leu Phe Met Val Thr Arg Ser Lys Asn Val Thr Val Arg Asp
225                 230                 235                 240
Leu Val Ile Leu Pro Gly Ser Val Asp Leu
                245                 250

<210> SEQ ID NO 4
<211> LENGTH: 534
<212> TYPE: PRT
<213> ORGANISM: Escherichia coli

<400> SEQUENCE: 4

Met Thr Ile Thr Lys Thr Val Ile Gly Val Asp Val Gly Ser Gly Ser
1               5                   10                  15
Val Arg Ala Gly Ile Phe Asp Leu Asn Gly Ser Leu Leu Ser His Ala
                20                  25                  30
Thr Glu Lys Ile Thr Thr Thr Arg Arg Ser Gly Ser Arg Val Glu Gln
            35                  40                  45
Ser Ser Gln Glu Ile Trp Gln Ala Val Cys Ser Cys Ile Arg Asn Ala
    50                  55                  60
Leu Thr Leu Ala Asp Val Cys Ala Gln Ser Val Ala Gly Ile Gly Phe
65                  70                  75                  80
Asp Ala Thr Cys Ser Leu Val Val Leu Asp Lys Asn Gly Asp Pro Leu
                85                  90                  95
Pro Val Ser Pro Glu Gly Asp Ala Lys Gln Asn Ile Ile Val Trp Met
                100                 105                 110
Asp His Arg Ala Thr Glu Gln Ala Glu Arg Ile Asn Ala Thr His His
            115                 120                 125
Pro Val Leu Asn Tyr Val Gly Gly Lys Ile Ser Pro Glu Met Glu Thr
        130                 135                 140
Pro Lys Ile Leu Trp Leu Lys Glu Asn Met Pro Glu Ile Tyr Glu Arg
145                 150                 155                 160
Ala Gly Gln Phe Phe Asp Leu Ala Asp Phe Leu Thr Trp Arg Ala Thr
                165                 170                 175
Gly Asp Leu Ala Arg Ser Val Cys Thr Val Thr Cys Lys Trp Thr Trp
            180                 185                 190
Leu Ala His Glu Asn Arg Trp Asp Pro Asp Tyr Phe Arg Thr Ile Gly
        195                 200                 205
Leu Ala Glu Leu Ala Asp Glu Asp Phe Ile Arg Ile Gly His His Ile
    210                 215                 220
Val Ser Pro Gly Thr Pro Cys Gly Asn Gly Leu Thr Ala Gln Ala Ala
225                 230                 235                 240
Ala Glu Met Gly Leu Leu Pro Gly Thr Pro Val Ala Val Gly Leu Ile
                245                 250                 255
Asp Ala His Ala Gly Ile Gly Thr Val Gly Val Glu Gly Gly Ala
            260                 265                 270
Leu Asn Asn Leu Ala Tyr Val Phe Gly Thr Ser Ser Cys Thr Met Ala
        275                 280                 285
Ser Thr Thr Ser Pro Ser Phe Val Pro Gly Val Trp Gly Pro Tyr Tyr
        290                 295                 300
Ser Ala Met Val Pro Gly Leu Trp Leu Val Glu Gly Gly Gln Ser Ala
305                 310                 315                 320
Ala Gly Ala Ala Ile Asp Gln Leu Leu Asp Phe His Pro Ala Val Glu
```

```
                     325                 330                 335
Glu Ala Arg Glu Met Ala Gln Arg Val Asn Gln Pro Leu Pro Val Trp
                340                 345                 350
Leu Ala Asp Arg Ile Leu Glu Lys Thr Ala Gln Pro Ser Asp Ala Val
            355                 360                 365
Ala Leu Ala Lys Gly Leu His Val Val Pro Glu Phe Leu Gly Asn Arg
        370                 375                 380
Ala Pro Phe Ala Asp Pro His Ala Arg Ala Val Ile Cys Gly Leu Gly
385                 390                 395                 400
Met Glu Arg Asp Leu Asp Asn Leu Leu Ala Leu Tyr Ile Ala Gly Leu
                405                 410                 415
Cys Gly Ile Gly Tyr Gly Leu Arg Gln Ile Leu Asp Ala Gln Thr Ala
                420                 425                 430
Gln Gly Val Val Ser Lys Asn Ile Val Ile Ser Gly Ala Gly Gln
        435                 440                 445
His Pro Leu Val Arg Gln Ile Leu Ala Asp Thr Cys Gly Ile Pro Val
    450                 455                 460
Ile Thr Thr Gln Cys Cys Glu Pro Val Leu Leu Gly Ser Ala Ile Leu
465                 470                 475                 480
Gly Ala Val Ala Gly Asn Ile Ala Pro Ser Val Gly Glu Ala Met Gln
                485                 490                 495
Gln Phe Thr His Val Asp Lys Tyr Tyr Tyr Pro Gln Glu Arg Tyr Gln
                500                 505                 510
Ser Leu His His Arg Arg Tyr Glu Ala Tyr Lys Gln Leu Gln His Thr
            515                 520                 525
Ala Lys Leu Leu Arg Asp
        530

<210> SEQ ID NO 5
<211> LENGTH: 424
<212> TYPE: PRT
<213> ORGANISM: Escherichia coli

<400> SEQUENCE: 5

Met Ser Arg Asn Asn Lys Gln Trp Leu Gly Leu Pro Leu His Leu Ile
1                5                  10                  15
Trp Gly Tyr Ile Ala Ile Ala Val Phe Met Thr Gly Asp Gly Phe Glu
                20                  25                  30
Leu Ala Phe Leu Ser His Tyr Ile Lys Ser Leu Gly Phe Thr Pro Ala
            35                  40                  45
Glu Ala Ser Phe Ala Phe Thr Leu Tyr Gly Leu Ala Ala Ala Leu Ser
        50                  55                  60
Ala Trp Val Ser Gly Val Val Ala Glu Ile Ile Thr Pro Gln Lys Thr
65                  70                  75                  80
Met Leu Ile Gly Phe Val Leu Trp Cys Val Phe His Val Leu Phe Leu
                85                  90                  95
Val Phe Gly Leu Gly Gln Ala Asn Tyr Gly Leu Ile Leu Leu Phe Tyr
            100                 105                 110
Gly Ile Arg Gly Leu Ala Tyr Pro Leu Phe Leu Tyr Ser Phe Ile Val
        115                 120                 125
Val Ile Ile His Asn Val Arg Ser Glu Asn Ser Ser Ala Leu Gly
    130                 135                 140
Trp Tyr Trp Ala Val Tyr Ser Val Gly Ile Gly Val Ala Gly Ser Tyr
145                 150                 155                 160
```

-continued

```
Ile Pro Ser Phe Thr Ile Pro Ile Met Gly Glu Met Gly Thr Leu Trp
                165                 170                 175

Leu Ala Leu Ala Phe Cys Phe Ala Gly Gly Val Ile Ala Met Ile Ser
                180                 185                 190

Leu Arg His Val Lys Thr Pro Gly His Met His Asn Leu Thr Pro Arg
        195                 200                 205

Glu Lys Phe Ala Glu Leu Ser Arg Ala Val Thr Leu Leu Tyr Thr Asn
    210                 215                 220

Arg Asn Ile Phe Leu Ser Ser Ile Val Arg Ile Ile Asn Thr Leu Ser
225                 230                 235                 240

Leu Phe Gly Phe Ala Val Ile Met Pro Met Met Phe Val Asp Glu Leu
                245                 250                 255

Gly Phe Thr Thr Ser Glu Trp Leu Gln Val Trp Ala Ala Phe Phe Phe
                260                 265                 270

Thr Thr Ile Phe Ser Asn Ile Phe Trp Gly Ile Val Ala Glu Lys Met
                275                 280                 285

Gly Trp Met Arg Val Ile Arg Trp Phe Gly Cys Leu Gly Met Ala Ala
        290                 295                 300

Ser Ser Leu Ala Phe Tyr Tyr Met Pro Gln Tyr Phe Gly His Asn Tyr
305                 310                 315                 320

Trp Met Ala Met Ile Pro Ala Ile Ala Leu Gly Thr Phe Val Ala Ala
                325                 330                 335

Phe Val Pro Met Ala Ala Val Phe Pro Ala Leu Glu Pro Lys His Lys
                340                 345                 350

Gly Ala Ala Ile Ser Val Tyr Asn Leu Ser Ala Gly Met Ser Asn Phe
        355                 360                 365

Leu Ala Pro Ala Ile Ala Val Val Leu Leu Pro Trp Phe Ser Thr Ile
    370                 375                 380

Gly Val Val Ile Ala Tyr Thr Ala Leu Tyr Leu Leu Ala Phe Val Leu
385                 390                 395                 400

Cys Ala Phe Ile Arg Val Glu Gln Pro Gly Phe Ser Ser Ala Pro Val
                405                 410                 415

Thr Glu Lys Ala Leu Asn Ile Ser
                420
```